United States Patent [19]

Hunt

[11] 4,145,430
[45] Mar. 20, 1979

[54] BETA-LACTAM COMPOUNDS, PREPARATION AND USE

[75] Inventor: Eric Hunt, Betchworth, England

[73] Assignee: Beecham Group Limited, United Kingdom

[21] Appl. No.: 921,738

[22] Filed: Jul. 3, 1978

[30] Foreign Application Priority Data

Jul. 23, 1977 [GB] United Kingdom .............. 31015/77

[51] Int. Cl.² .................. C07D 498/04; A61K 31/42
[52] U.S. Cl. .............................. 424/272; 260/307 DB; 260/307 FA; 424/246; 424/271
[58] Field of Search ....................... 424/272, 246, 271; 260/307 F, 307 FA

[56] References Cited

U.S. PATENT DOCUMENTS 4,093,626  6/1978  Hunt ............................. 260/307 FA Primary Examiner—Raymond V. Rush
Attorney, Agent, or Firm—Jacobs & Jacobs

[57] ABSTRACT

The compounds of the formula (I):

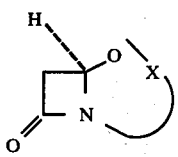

(I)

wherein X represents a moiety of the sub-formula (a) or (b):

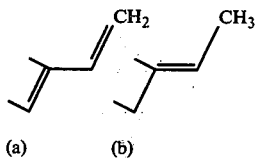

have been found to be β-lactamase inhibitors which may be used in pharmaceutical compositions to enhance the effectiveness of penicillins or cephalosporins. The diene of the formula (I) may be produced by the decarboxylation of clavulanic acid or a derivative thereof and the monoene of the formula (I) may be produced by the 1,4 addition of hydrogen to the diene of the formula (I). The diene is thus also useful as a chemical intermediate and other such uses are demonstrated.

20 Claims, No Drawings

BETA-LACTAM COMPOUNDS, PREPARATION AND USE

The present invention relates to β-lactam containing compounds, to the process for their preparation, to pharmaceutical compositions containing them and to their use as intermediates and synergists.

Belgian Patent No. 840,252 disclosed the compounds of the formula (II):

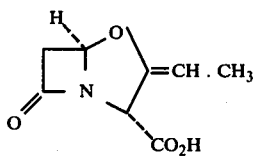

and their salts. Such compounds were shown to possess β-lactamase inhibitory activity which enables them to enhance the effectiveness of penicillins and cephalosporins against β-lactamase producing bacteria. Belgian Pat. No. 847,044 disclosed inter alia that esters of the compound of the formula (III):

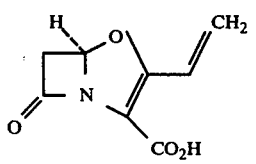

may be used to prepare compounds such as esters of 9-dibenzylaminodeoxyclavulanic acid. Belgian Patent No. 849,308 disclosed that the esters of the compound of the formula (III) also possessed β-lactamase inhibitory activity.

It is believed desirable to produce compounds having differing β-lactamase inhibitory properties or which may be used as intermediates to compounds having such properties. Such compounds have been discovered.

The present invention provides the compounds of the formula (I):

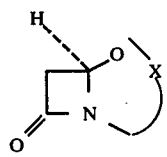

wherein X represents a moiety of the sub-formula (a) or (b):

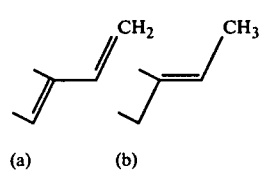

The monoenes within formula (I), that is the compounds of the formula (IV):

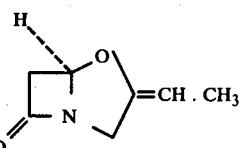

are envisaged as β-lactamase inhibitors which may be used to enhance the effectiveness of penicillins or cephalosporins. When making use of this property the E-isomer of the compound may be used or the Z-isomer of the compound may be used or mixtures of the E- and Z-isomers may be used.

The diene within formula (I), that is the compound of the formula (V):

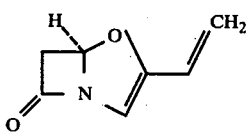

is also envisaged as a β-lactamase inhibitor which may be used to enhance the effectiveness of penicillins or cephalosporins but its chemical reactivity also makes it a useful intermediate, for example it is able to take place in 1,4-addition reactions as will become apparent hereinafter.

For use for any of the preceding utilities it is most suitable that the compounds of the formulae (I), (IV) or (V) are at least 50% w/w pure so that unwanted effects due to possible by-products of their formation are reduced. (The % purity is calculated on a solvent free basis since it is conventional to prepare and isolate the compound of the formula (V) in an organic solvent.) Compounds that are at least 80% w/w pure are also contemplated.

The present invention also provides a process for the preparation of the compounds of the formula (IV) which process comprises the hydrogenation of the compound of the formula (V) in the presence of a palladium or platinum catalyst.

Most suitably an approximately atmospheric pressure of hydrogen is employed. Most suitably palladium on charcoal is used as catalyst, for example 10% palladium on charcoal. The reaction will be carried out in an inert organic solvent, for example in tetrahydrofuran or other similar solvent.

The hydrogenation reaction normally produces a mixture of E- and Z-isomers of the compound of the formula (IV). These isomers may be separated chromatographically if desired, for example by preparative high pressure liquid chromatography or column chromatography.

The hydrogenation of the compound of the formula (V) exemplifies the 1,4-addition reactions (in this case the 1,4-addition of a molecule of hydrogen) to which the compound of the formula (V) is susceptible. The use of the compound of the formula (V) as a chemical intermediate, particularly for 1,4-addition reaction, forms a part of this invention.

This invention also provides a process for the preparation of the compound of the formula (V) which process comprises the reaction of clavulanic acid with either (a) a compound of the formula (VI):

where R' is a lower alkyl group; or
(b) a compound of the formula (VII):

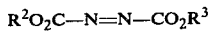 (VII)

wherein $R^2$ and $R^3$ are each independently lower alkyl, lower alkylaryl or aryl groups; and a compound of the formula (VIII):

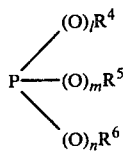 (VIII)

wherein l, m and n are each independently 0 or 1 and $R^4$, $R^5$ and $R^6$ are each independently a lower alkyl, lower alkylaryl or aryl group.

Suitable values for R' include alkyl of 1–6 carbon atoms such as the groups of the formula $-CH_2)_qCH_3$ wherein q is 1, 2, 3, 4 or 5. Most suitably q is 1 or 2. Preferably q is 1.

Suitable compounds of the formula (VII) include those wherein $R^2$ and $R^3$ are independently selected from benzyl, phenyl or alkyl groups of up to 6 carbon atoms. Particularly suitable $R^2$ and $R^3$ represent the same moiety, for example both represent methyl, ethyl, propyl or butyl groups. Particularly suitable compounds of the formula (VII) include those therein $R^2$ and $R^3$ each represent an ethyl or t-butyl group.

Suitable compounds of the formula (VIII) include those therein $R^4$, $R^5$ and $R^6$ are selected from methyl, ethyl, n-propyl, n-butyl, benzyl, phenyl and methoxyphenyl groups. It is generally convenient that $R^4$, $R^5$ and $R^6$ each represent the same moiety. Particularly suitable compounds of the formula (VIII) include triphenylphosphine, trimethylphosphite and triethylphosphite. A preferred compound of the formula (VIII) is triphenylphosphine.

The compound of the formula (V) tends to polymerise when free of solvent at room temperature so that it must either be stored in solution (optionally with hydroquinone) or at a low temperature. Preferably the compound of the formula (V) is used shortly after its preparation.

The reaction of clavulanic acid with the compound of the formula (VI) takes place in an inert organic solvent such as tetrahydrofuran, 1,2-dimethoxyethane, ethyl acetate, tetrahydrofuran/toluene, tetrahydrofuran/benzene or solvents of similar properties. The reaction will generally take place at a non-extreme temperature such as $-30°$ C. to $40°$ C., for example $0°$ C. to $25°$ C. It is generally most convenient to carry out the reaction at ambient temperature.

The reaction of clavulanic acid with the compounds of the formula (VII) and (VIII) will take place in an inert organic solvent such as tetrahydrofuran, 1,2-dimethoxyethane or solvent of similar properties. The reaction will generally take place at $10°$ C. to $40°$ C. It is generally most convenient to carry out the reaction at ambient temperature.

In both preceding reactions it is preferable that the reaction medium is maintained free of hydroxylic materials other than clavulanic acid.

The present invention also provides a process for the preparation of a compound of the formula (V) which comprises maintaining a salt of an O-acyl derivative of clavulanic acid at a non-extreme temperature in solution in an aqueous ether.

Suitable derivatives of clavulanic acid for use in this process include the acetyl derivative, for example as its potassium salt. Acylated derivatives of clavulanic acid are described in Belgian Pat. No. 834,645.

The decomposition process tends to be slow and low yielding so it is desirable to warm the reaction to above ambient temperature, for example to $30-45°$ C., to encourage reaction.

Suitable solvents include aqueous tetrahydrofuran and aqueous 1,2-dimethoxyethane.

The present invention also provides pharmaceutical compositions which comprise a compound of the formula (I) and a pharmaceutically acceptable carrier.

Most suitably the composition will comprise a compound of the formula (IV) which may be in the form of the Z-isomer, the E-isomer or, less favourably as a mixture thereof.

The compositions of the invention include those in a form adapted for oral or parenteral use and may be used for the treatment of the infection in mammals including humans. The infections to be treated include those due to gram-positive bacteria and gram-negative bacteria and less commonly fungal infections.

Suitable forms of the compositions of this invention include tablets, capsules, creams, syrups, suspensions, solutions, reconstitutable and sterile forms suitable for injection or infusion. Such compositions may contain conventional pharmaceutically acceptable materials such as diluents, colours, flavours, preservatives and the like in accordance with conventional pharmaceutical practice in the manner well understood by those skilled in the art of formulating liquid or oily pharmaceuticals.

Injectable or infusable compositions of a compound of the formula (I) are suitable. A sterile compound of the formula (I) may be sealed in a glass vial, bottle or the like and made up into an injectable solution by the addition of aqueous ethanol or the like.

Unit dose compositions comprising a compound of the formula (I) adapted for oral administration form a further preferred compositions aspect of this invention. Particularly favoured forms include soft gelatin capsules (with polyethyleneglycol) or other solid forms in which the compound of the formula (I) is absorbed on an inert carrier such as lactose, starch or the like.

The compound of the formula (I) may be present in the composition as sole therapeutic agent or it may be present together with other therapeutic agents such as a β-lactam antibiotic. Suitable β-lactam antibiotics for inclusion in the compositions of this invention include benzylpenicillin, phenoxymethylpenicillin, carbenicillin, azidocillin, propicillin, ampicillin, amoxycillin, epicillin, ticarcillin, cyclacillin, cefatriazine, pirbenicillin, α-sulphonyloxybenzylpenicillin, cephaloridine, cephalothin, cefazolin, cephalexin, cephacetrile, cephamandole, nafate, cephapirin, cephradine, 4-hydroxy-cephalexin, cefaparole, cephaloglycine and other well known penicillins and cephalosporins or pro-drugs therefor.

Naturally if the penicillin or cephalosporin present in the composition is not suitable for oral administration then the composition will be adapted for parenteral administration.

When present together with a cephalosporin or penicillin, the ratio of a compound of the formula (I) present to the other antibacterial agent may vary over a wide range of ratios, for example 3:1 to 1:10 and advantageously may be from 1:1 to 1:8, for example, 1:2, 1:3, 1:4, 1:5 or 1:6.

The total quantity of compound of the formula (II) in any unit dosage form will normally be between 25 and 1000 mg and will usually be between 50 and 500 mg, for example 62.5, 100, 125, 150, 200 or 250 mg.

Compositions of this invention may be used for the treatment of infections of inter alia, the respiratory tract, the urinary tract and soft tissues and mastitis in cattle.

Normally between 50 and 1000 mg of the compounds of this invention will be administered each day of treatment but more usually between 100 and 750 mg of the compounds of the invention will be administered per day, for example as 1–6 doses, more usually 2–4 doses.

EXAMPLE 1

(5R)-7-oxo-3-vinyl-4-oxa-1-azabicyclo[3.2.0]hept-2-ene

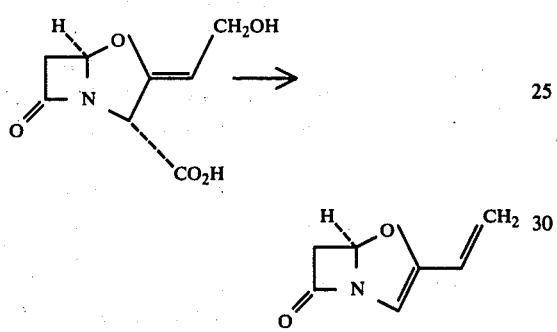

Clavulanic acid (3.5 mmole) in dry tetrahydrofuran (5 ml) and N,N-dimethylformamide dimethyl acetal (4.0 mmole) in dry toluene (5 ml) were added dropwise and simultaneously to a well stirred mixture of dry toluene (10 ml) and dry tetrahydrofuran (10 ml) containing hydroquinone (ca 3 mg). After addition was complete (5 minutes), the mixture was stirred for an additional 5 minutes, and was then decolourised using charcoal (ca 0.5 g) and filtered. The filter was washed with dry toluene (20 ml) and the combined filtrate and washings were concentrated to ca 10 ml under reduced pressure. The concentrated solution was made up to 70 ml using dry toluene. From an aliquot (8 ml) of this solution the solvent was removed under reduced pressure to yield a yellow oil (55 mg) which was immediately redissolved in CDCl$_3$ (1 ml). An nmr spectrum of this solution showed absorptions for only the title compound, dimethylformamide, and toluene. On the basis of this the estimated yield of title compound was 2.9 mmole (83%).

When free of solvent the title compound readily polymerises. For determination of spectroscopic and biological properties aliquots of the toluene solution were treated in a manner similar to that described above for measurement of the nmr spectrum. The title compound was characterised by the following spectroscopic properties. $\lambda_{max}$ (EtOH): 277.5 nm. $\nu_{max}$ (CHCl$_3$): 1797 ($\beta$-lactam C=O), 1670 and 1640 (C=C)cm$^{-1}$. δ (CDCl$_3$): 3.36 (d, J 17Hz, 1H, C(6)H), 3.63 (dd, J 17, 2Hz, 1H, C(6)H), 5.22 (dd, J 10.5, 1.0Hz, 1H, olefinic H), 5.49 (dd, J 16, 1.0Hz, 1H, olefinic H), 5.80 (s, 2H, C(5)H and C(2)H), 6.10 (dd, J 16, 10.5Hz, 1H, olefinic H).

EXAMPLE 2

(5R)-7-oxo-3-vinyl-4-oxa-1-azabicyclo[3.2.0]hept-2-ene

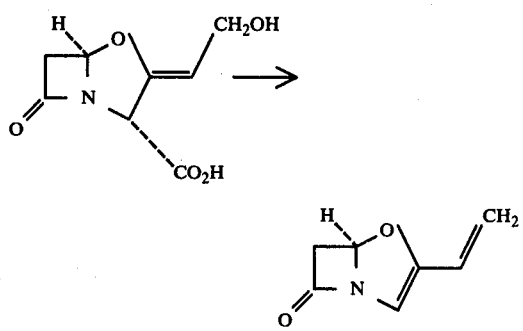

Clavulanic acid (1.5 mmole) in dry tetrahydrofuran (5 ml) under a dry nitrogen atmosphere was treated with triphenylphosphine (1.5 mmole) and then, dropwise, diethylazoxicarboxylate (1.5 mmole) in dry tetrahydrofuran (2 ml). After addition was complete (2 minutes), the mixture was stirred for 30 minutes at room temperature and was then ice-cooled and diluted with a mixture of ether and n-pentane (1:2, 20 ml). The mixture was filtered and the filtrate was diluted with dry benzene (10 ml) and then concentrated to about 5 ml under reduced pressure to yield a solution of the title compound (1 mmole).

EXAMPLE 3

(5R)-7-Oxo-3-vinyl-4-oxa-1-azabicyclo[3.2.0]hept-2-ene

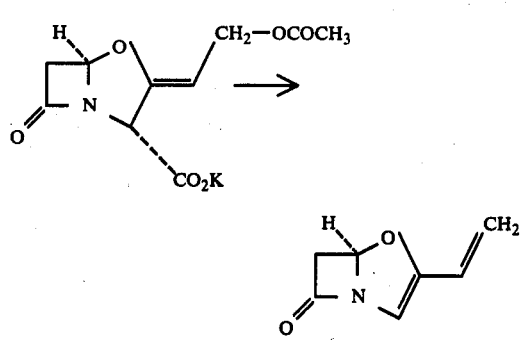

Benzyl 9-0-acetylclavulanate (90 mg., 0.27 mmole) was dissolved in tetrahydrofuran (10 ml) and the solution was shaken with 10% palladium-on-charcoal (30 mg) under one atmosphere of hydrogen at room temperature for 20 minutes. The catalyst was removed by filtration and was washed with tetrahydrofuran. The filtrate was concentrated to 5 ml by evaporation of solvent under reduced pressure to yield a solution of 9-0-acetylclavulanic acid in tetrahydrofuran.

To the above solution a solution of potassium carbonate (0.14 mmole) in water (1 ml) was added with stirring. The mixture was kept at room temperature for 2 hours, at which time the presence of the title compound was detected using t.l.c. (silica gel; 1:2 ethyl acetate/petrol). The mixture was warmed to 40° for a further 3 hours and was then diluted with ethyl acetate (30 ml). The tetrahydrofuran was evaporated under reduced pressure and then the aqueous layer was separated. The solution was dried (sodium sulphate) and concentrated to 3 ml by evaporation of solvent under reduced pressures to yield a solution containing 0.04 mmole of the title compound.

EXAMPLE 4

(5R)-3-ethylidene-4-oxa-1-azabicyclo[3.2.0]heptan-7-one

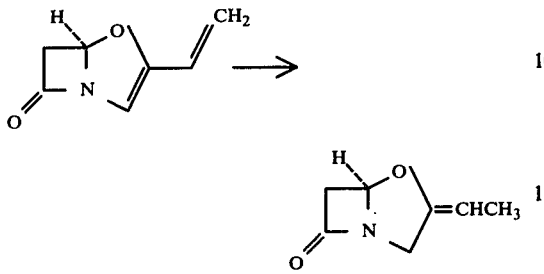

(5R)-7-Oxo-3-vinyl-4-oxa-1-azabicyclo 3.2.0 - hept-2-ene (2.4 mmole) in tetrahydrofuran (30 ml) was shaken with 10% palladium on charcoal (120 mg) under one atmosphere of hydrogen for 2 hours. The catalyst was then removed by filtration and was washed well with fresh tetrahydrofuran. From the filtrate and washings the solvent was removed under reduced pressure and the residue chromatographed on silica gel (15 g) using ethyl acetate/petroleum ether. In this way a colourless oil (140 mg) was obtained which by nmr analysis contained the title compound (87%). $[\alpha]_D^{22} = +210.5°$ (c = 1.0, $CHCl_3$). $\nu_{max}$ ($CHCl_3$): 1790 ($\beta$-lactam C = O), 1705 (olefinic C = C)$cm^{-1}$.

The $I_{50}$ values obtained for the product of this example against certain common gram positive and gram negative bacteria were as follows:

| $\beta$-lactamase from | Enterobacter cloacae P 99 | Ps. aeruginosa |
|---|---|---|
| $I_{50}$ (g/ml) | 0.28 | 0.86 |
| $\beta$-lactamase from | E. coli JT 4 | Proteus mirabilis C 889 |
| $I_{50}$ ($\mu$g/ml) | 0.22 | 1.6 |
| $\beta$-lactamase from | Staphylococcus aureus Russell | |
| $I_{50}$ ($\mu$g/ml) | 0.31 | |

EXAMPLE 5

Z-(5R)-3-ethylidene-4-oxa-1-azabicyclo[3.2.0]heptan-7-one

E-(5R)-3-ethylidene-4-oxa-1-azabicyclo[3.2.0]heptan-7-one

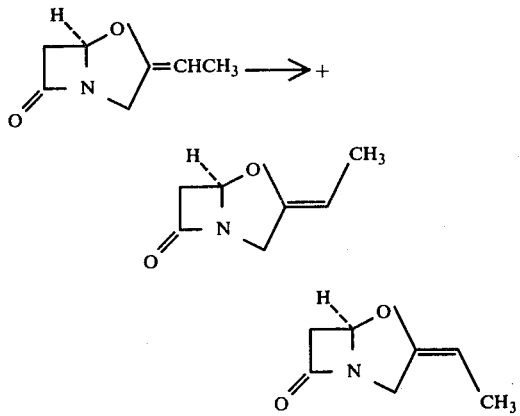

The product of Example 4 (60 mg) was subjected to high pressure liquid chromatography under the following conditions:

Column: Magnum 9, 20 cm × ½", 10µSiO₂
Solvent: 1/9 Ethyl acetate/cyclohexane
Flow rate: 4 ml per minute
Detector: 270 nm
Loading: 100 µl of 5% solution in solvent The Z-isomer under these conditions had a retention time of 10 minutes which allowed easy separation from the E-isomer which had a 12 minute retention time. The isomers were obtained by evaporation of the solvent: Z-isomer (33 mg), E-isomer (8 mg).

The Z-isomer was obtained as a colourless oil; $[\alpha]_D^{22} = +185.1°$ (c 1.0, $CHCl_3$); $\nu_{max}$ ($CHCl_3$); 1790 ($\beta$-lactam C=O) and 1702 (olefinic C=C) $cm^{-1}$. $\delta$ ($CDCl_3$): 1.60 (dt, J 7, 2Hz, 3H), 2.91 (d, J 16Hz, 1H), 3.35 (dd, J16, 2Hz, 1H), 3.45 (br.d, J 16Hz, 1H), 4.1–4.4 (complex, 2H), 5.39 (d, J 2Hz, 1H). m/e: 139 (M⁺, 88%), 111 (7), 97 (43), 96 (15), 83 (45), 82 (18), 70 (56), 68 (46). 55 (100), 54 (52).

The E-isomer was obtained as colourless crystals, $[\alpha]_D^{22} = +219°$ (c 1.0, $CHCl_3$); $\nu_{max}$ $CHCL_3$): 1790 ($\beta$-lactam C=O), 1705 (olefinic C=C)$cm^{-1}$. $\delta$ ($CDCl_3$): 1.46 (br.d, J 6Hz, 3H), 2.88 (d, J 16Hz, 1H), 3.30 (dd, J 16, 2Hz, 1H), 3.45 (br. d, J 15Hz, 1H), 4.30 (br.d, J 15Hz, 1H), 4.83 (m, 1H), 5.32 (d, J 2Hz, 1H). m/e: 139 (M⁺, 58%), 111 (5), 97 (28), 96 (5), 83 (40), 82 (20), 70 (35), 68 (32), 55 (100), 54 (36).

EXAMPLE 6

(5R)-3-Ethylidene-4-oxa-1-azabicyclo[3.2.0]heptan-7-one (5R)-7-oxo-3-vinyl-4-oxa-1-azabicyclo[3.2.0]hept-2-ene (2.4 mmole) in tetrahydrofuran (20 ml) was shaken with 5% platinum on charcoal (150 mg) under 1 atmosphere of hydrogen at room temperature for 1.5 hours. The catalyst was removed by filtration and was washed with tetrahydrofuran. The solvent was evaporated from the filtrate and the residue was chromatographed on silica gel using 1:7 ethyl acetate/petroleum ether (b.p. 60–80°). A mixture of E- and Z- isomers of the title compound was thus obtained as a colourless oil (40 mg).

EXAMPLE 7

(5R)-10,10',11,11'-Tetracyano-3-oxo-6-oxa-2-azatricyclo-[5,4,0.0$^{2,5}$]undec-7,8-ene

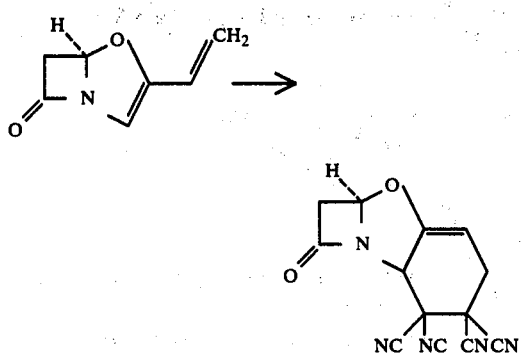

To the solution from Example 3 tetracyanoethylene (40 mg) was added and the mixture was kept at room temperature for 16 hours. The solvent was evaporated under pressure and the residue was chromatographed on silica gel (5 g) using 1:4→1:1 ethyl acetate/petroleum ether (b.p. 60–80°). The title compound was thus obtained as colourless crystals (10 mg., 0.038 mmole); recrystallisation from ethyl acetate/petroleum ether (b.p. 60–80°) gave colourless rods (8 mg) m.p. 200–202°.

EXAMPLE 8

3,5,14-Trioxo-4,10-dioxa-15-azatetracyclo[7.5.0.0$^{2,6}$.0.$^{11,15}$]pentadec-8,9-ene

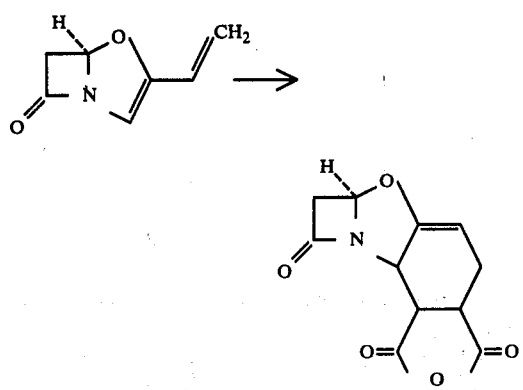

To the solution from Example 2, maleic anhydride (2 mmole) was added and the mixture was kept at room temperature for 18 hours. Evaporation of solvent under reduced pressure followed by chromatography on silica gel (20 g) using ethyl acetate/petroleum ether gave the title compound as colourless crystals (170 mg., 0.72 mmole), m.p. 148–150°. Recrystallisation from ethyl acetate/petroleum ether (b.p. 60–80°) gave colourless rods, m.p. 157–159°. (Found: C, 56.18; H, 3.69; N, 5.92. C$_{11}$H$_9$NO$_5$ requires C, 56.18; H, 3.86; N, 5.96%). $[\alpha]_D^{20}$ = +404° (c 0.75, CHCl$_3$). $\nu_{max}$ (CHCl$_3$): 1740 (anhydride C=O), 1800 (sh., β-lactam C=O), 1783 (anhydride C=O), 1690 (olefinic C=C cm$^{-1}$. δ (CDCl$_3$): 2.30 (m, 1H), 2.73 (ddd, J 15, 7, 1Hz, 1H) 3.02 (d, J 16Hz, 1H), 3.25–3.75 (complex, 3H), 4.42 (br. d, J 6Hz, 1H), 5.13 (m, 1H), 5.45 (d, J 2Hz, 1H).

DEMONSTRATION 1

Biological activity for (5R)-7-oxo-3-vinyl-4-oxa-1-azabicyclo[3.2.0]hept-2-ene

The compound from Example 1 was a potent inhibitor of β-lactamase enzymes as illustrated in the following Table. I$_{50}$ values were determined using the process described in Belgium Pat. No. 827,926.

| Source of β-lactamase | I$_{50}$ (μg/ml) |
|---|---|
| Enterobacter cloacae P99 | 0.026 |
| Pseudomonas aeruginosa A | 0.06 |
| Proteus mirabilis C889 | 0.058 |
| E. coli JT4 | 0.056 |
| Ps. aeruginosa Dalgleish | 0.04 |
| Staph. aureus Russell | <0.08 |

The compound displayed antibacterial activity as shown in the following Table:

| | M.I.C. (μg/ml) |
|---|---|
| Staphylococcus aureus Russell | 125 |
| Klebsiella aerogenes E70 | 125 |
| Proteus mirabilis C889 | 125 |
| E. coli JT39 | 125 |
| Pseudomonas aeruginosa Dalgleish | 125 |
| E. coli JT410 | 125 |

The compound synergised the antibacterial activity of ampicillin as shown in the following Table:

| Concentration of compound from | M.I.C. for Ampicillin (μg/ml) | | |
|---|---|---|---|
| Example 1 (μg/ml) | Staph. aureus Russell | Kleb. aerogenes E70 | E. coli JT39 |
| none | 500 | 500 | >500 |
| 5 | 5 | 12.5 | 62.5 |
| 20 | 1.25 | 6.2 | 8 |

DEMONSTRATION 2

Synergistic activity for E- and Z-(5R)-3-ethylidene-4-oxa-1-azabicyclo[3.2.0]heptan-7-one The Z-isomer synergised the antibacterial activity of ampicillin as shown in the following Table:

| Concentration of | M.I.C. for ampicillin (μg/ml) | | |
|---|---|---|---|
| Z-isomer (μg/ml) | Staph. aureus Russell | Kleb. aerogenes E70 | E. coli JT |
| None | 500 | 500 | 2000 |
| 5 | 5 | 50 | 62 |
| 20 | 2.5 | 12.5 | 62 |

The Z-isomer also synergised the antibacterial activity of caphaloridine. For example, when combined with the Z-isomer at a level of 20 μg/ml, the M.I.C. of cephaloridine against E. coli JT410 was lowered from 125 μg/ml to 8 μg/ml.

The E-izomer is able to synergise the antibacterial activity of ampicillin. Thus, when present with the E-izomer at a level of 20 μg/ml, the M.I.C. of ampicillin against Staph. aureus Russell was lowered from 500 μg/ml to 3.1 μg/ml.

Antifungal activity

The Z-isomer is able to inhibit the growth of *Candida albicans*. Thus, a loading of 250 μg of the Z-isomer on a paper tape which was contacted with a blood agar base plate seeded with *Candida albicans* BRL 1003 and incubated at 28° C. for 24 hours produced a zone of inhibition with diameter 22.1 mm.

DEMONSTRATION 3

Acute toxicity in mice for
(5R)-3-ethylidene-4-oxa-1-azabicyclo[3.2.0]heptan-7-one

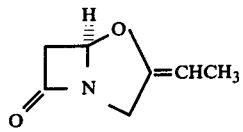

The compound from Example 4 (containing 26% E-isomer and 62% Z-isomer) was tested for acute toxicity in mice as described below.

Routes: subcutaneous (s.c.) and intraperitoneal (i.p.)
Dosages: 1000, 500 and 250 mg/kg s.c. and 500 mg/kg i.p. as solutions in 1:4 dimethylsulphoxide/water.

| Dosage (mg/kg) | Route | No. of Mice in group | No. of Mice Alive | | | | |
|---|---|---|---|---|---|---|---|
| | | | Day 1 | Day 2 | Day 4 | Day 6 | Day 8 |
| 1000 | s.c. | 5 | 4 | 4 | 4 | 4 | 4 |
| 500 | s.c. | 5 | 5 | 5 | 5 | 5 | 5 |
| 250 | s.c. | 5 | 5 | 5 | 5 | 5 | 5 |
| 500 | i.p. | 1 | 1 | 1 | 1 | 1 | 1 |

I claim:

1. A compound of the formula (I)

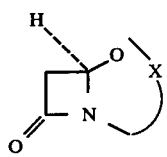

wherein X is a moiety of the sub-formula (a) or (b):

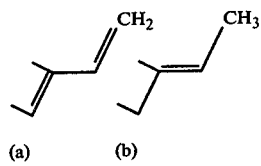

2. A compound according to claim 1 of the formula (IV):

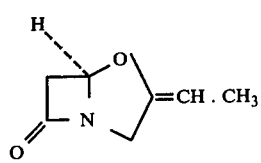

3. A compound according to claim 2 in the form of the E-isomer.

4. A compound according to claim 2 in the form of the Z-isomer.

5. A compound according to claim 2 in the form of a mixture of E- and Z-isomers.

6. A compound according to claim 1 of the formula (V):

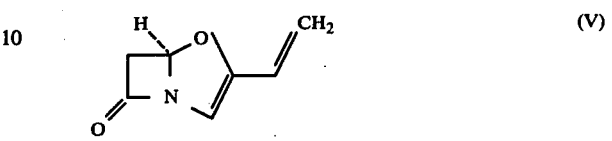

7. A compound according to claim 1 which is at least 50% w/w pure.

8. A compound according to claim 1 which is at least 80% w/w pure.

9. A pharmaceutical composition which comprises an antibacterially effective amount amount of a compound of the formula (I):

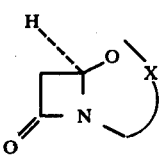

wherein X is a moiety of the sub-formula (a) or (b):

in combination with a pharmaceutically acceptable carrier.

10. A pharmaceutical composition according to claim 9 wherein the compound is of the formula (IV):

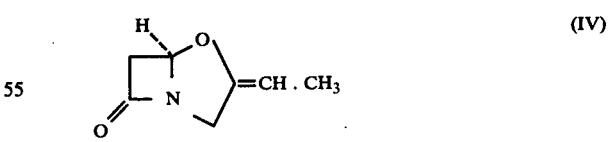

11. A composition according to claim 10 wherein the compound is in the form of the E-isomer.

12. A composition according to claim 10 wherein the compound is in the form of the Z-isomer.

13. A composition according to claim 10 wherein the compound is in the form of a mixture of E- and Z-isomers.

14. A composition according to claim 9 wherein the compound is of the formula (V):

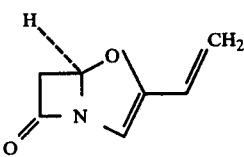

15. A method of treating bacterial infections in humans and animals which comprises administering to a human or animal in need thereof an antibacterially effective amount of a compound of the formula (I):

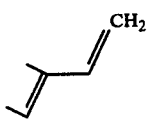

wherein X is a moiety of the sub-formula (a) or (b):

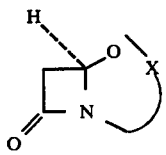 (a)

or

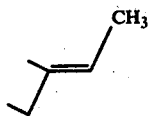 (b)

16. A method according to claim 15 wherein the compound is of the formula (IV):

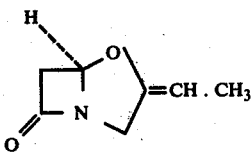 (IV)

17. A method according to claim 16 wherein the compound is in the form of the E-isomer.
18. A method according to claim 16 wherein the compound is in the form of the Z-isomer.
19. A method according to claim 16 wherein the compound is in the form of a mixture of E- and Z-isomers.
20. A method according to claim 15 wherein the compound is of the formula (V):

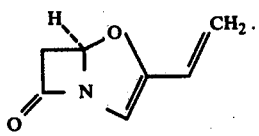 (V)

* * * * *